(«12») United States Patent
Abri et al.

(10) Patent No.: US 9,122,142 B2
(45) Date of Patent: Sep. 1, 2015

(54) DISPLAY APPARATUS FOR AN OPERATING ROOM

(75) Inventors: Omid Abri, Berlin (DE); Stephan Schrader, Kleinmachnow (DE); Julian Verkin, Neuendorf (DE); Thorsten Karge, Berlin (DE)

(73) Assignee: Karl Storz GmbH & Co. KG (DE)

( * ) Notice: Subject to any disclaimer, the term of this patent is extended or adjusted under 35 U.S.C. 154(b) by 423 days.

(21) Appl. No.: 13/434,333

(22) Filed: Mar. 29, 2012

(65) Prior Publication Data

US 2012/0249977 A1    Oct. 4, 2012

(30) Foreign Application Priority Data

Mar. 30, 2011   (DE) .......................... 10 2011 001 681
May 24, 2011   (DE) .......................... 10 2011 076 316

(51) Int. Cl.
| | |
|---|---|
| G03B 21/14 | (2006.01) |
| G03B 21/22 | (2006.01) |
| G03B 21/56 | (2006.01) |
| G03B 21/58 | (2014.01) |
| G03B 21/00 | (2006.01) |
| G03B 21/10 | (2006.01) |
| G03B 21/16 | (2006.01) |
| A61G 12/00 | (2006.01) |
| G03B 21/30 | (2006.01) |

(Continued)

(52) U.S. Cl.
   CPC .............. *G03B 21/58* (2013.01); *A61G 12/004* (2013.01); *G03B 21/00* (2013.01); *G03B 21/10* (2013.01); *G03B 21/16* (2013.01); *A61B 2019/5229* (2013.01); *A61G 13/107* (2013.01); *G02F 1/1333* (2013.01); *G02F 1/13336* (2013.01); *G03B 21/30* (2013.01); *G03B 21/56* (2013.01); *H01L 27/3293* (2013.01)

(58) Field of Classification Search
   CPC ...... G03B 21/56; G03B 21/30; G03B 21/145; G03B 21/58; A61B 1/00048; A61B 2019/5229
   USPC .............. 353/122, 119, 71, 72; 359/449, 451, 359/461; 160/229.1
   See application file for complete search history.

(56) References Cited

U.S. PATENT DOCUMENTS 2,827,955 A  *  3/1958  Hurley ........................... 160/369
3,632,185 A  *  1/1972  Meanor .......................... 359/451
(Continued)

FOREIGN PATENT DOCUMENTS

| DE | 19516189 A1 | 11/1996 |
|---|---|---|
| DE | 19719349 A1 | 7/1998 |

(Continued)

OTHER PUBLICATIONS

Hubbold, et al.; "Stereoscopic Volume Rendering"; Jan. 1, 1998; pp. 105-115 (11 pages); Internet Citation: URL http://citeseerx.ist.psu.edu/viewdoc/summary?doi=10.1.1.35.4700.

(Continued)

*Primary Examiner* — William C Dowling
*Assistant Examiner* — Ryan Howard
(74) *Attorney, Agent, or Firm* — Whitmyer IP Group LLC

(57) ABSTRACT

A display apparatus for displaying medical information in a medical treatment facility includes an image surface to depict information, such that the image surface is configured so that it can be converted by reshaping from an operating condition into a resting condition and vice versa.

14 Claims, 7 Drawing Sheets

(51) Int. Cl.
   *A61G 13/10* (2006.01)
   *A61B 19/00* (2006.01)
   *G02F 1/1333* (2006.01)
   *H01L 27/32* (2006.01)

(56) References Cited

U.S. PATENT DOCUMENTS

| | | | |
|---|---|---|---|
| 3,931,452 | A | 1/1976 | Nilsson |
| 6,175,610 | B1 | 1/2001 | Peter |
| 6,449,103 | B1 | 9/2002 | Charles |
| 6,637,896 | B2 * | 10/2003 | Li et al. ............... 353/119 |
| 8,024,881 | B2 * | 9/2011 | Redmon ............... 40/610 |
| 2003/0218720 | A1 | 11/2003 | Morita et al. |
| 2006/0023450 | A1 * | 2/2006 | Chung et al. ............... 362/246 |
| 2006/0250692 | A1 | 11/2006 | Peterson et al. |
| 2009/0102915 | A1 * | 4/2009 | Arsenich ............... 348/53 |
| 2009/0128785 | A1 * | 5/2009 | Silverstein ............... 353/119 |
| 2009/0201434 | A1 * | 8/2009 | Yuzawa ............... 348/838 |
| 2010/0201604 | A1 | 8/2010 | Kee et al. |

FOREIGN PATENT DOCUMENTS

| | | |
|---|---|---|
| DE | 29903798 U1 | 5/1999 |
| DE | 20001134 U1 | 5/2000 |
| EP | 0674881 A1 | 10/1995 |
| EP | 2061261 A1 | 5/2009 |
| GB | 486200 A | 5/1938 |
| GB | 2468922 A | 9/2010 |
| JP | 2005318937 A | 11/2005 |
| JP | 2010046194 A | 3/2010 |
| KR | 20110016748 A | 2/2011 |
| WO | 0137070 A2 | 5/2001 |
| WO | 0186575 A2 | 11/2001 |
| WO | 0229490 A1 | 4/2002 |
| WO | 2007141933 A1 | 12/2007 |

OTHER PUBLICATIONS

German Search Report; Application No. DE 10 2011 076 316.3; Issued: Jan. 13, 2011; 6 pages.

* cited by examiner

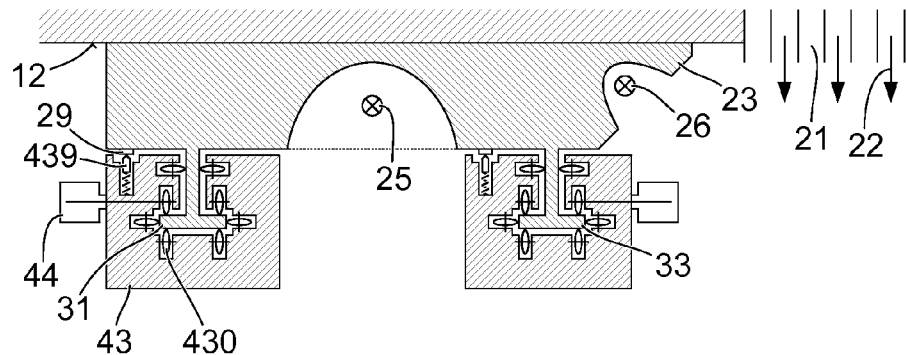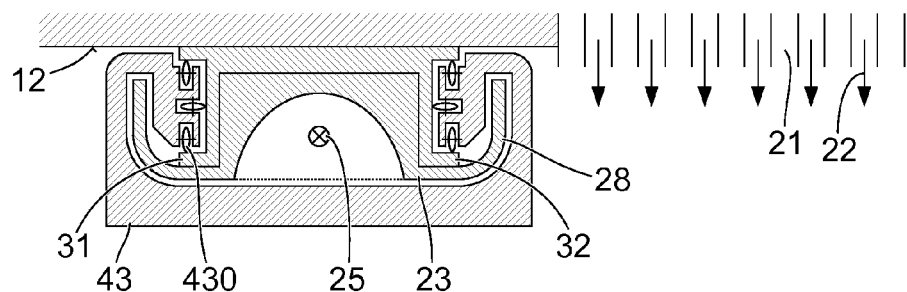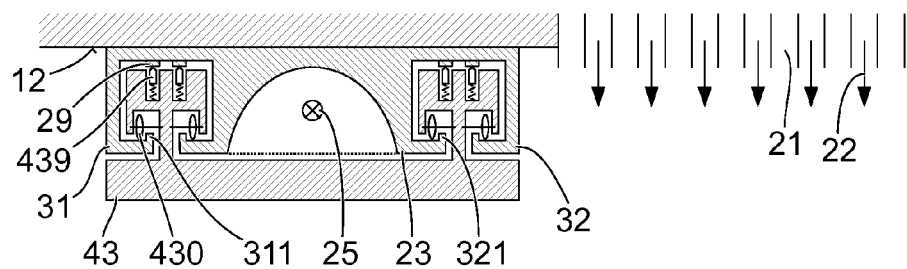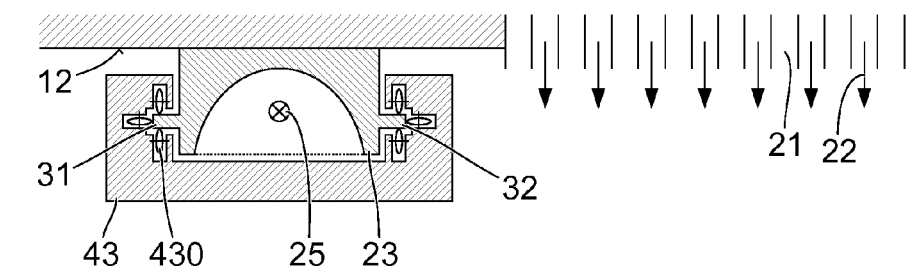

DISPLAY APPARATUS FOR AN OPERATING ROOM

CROSS-REFERENCE TO RELATED APPLICATIONS

The present application claims priority of German Patent Application Nos. 10 2011 001 681.3 filed on Mar. 30, 2011 and 10 2011 076 316.3 filed on May 24, 2011, the content of which is incorporated herein by reference.

FIELD OF THE INVENTION

The present invention relates to a display device for an operating room or another medical treatment facility.

BACKGROUND OF THE INVENTION

The number of devices and systems that are provided in a modern operating room or other medical treatment facility for diagnostic or therapeutic purposes has constantly increased over time. The functions provided by these devices and systems are increasing, and the quantity of information made available to surgical and other staff, and required to be processed by them, is also growing. Therefore there are efforts to integrate functions previously fulfilled by numerous separate devices into fewer devices and systems; to improve the arrangement of devices and systems; to display information, which previously was provided at different locations, in a common location and geared as far as possible to a specific situation, in particular on viewing screens of constantly increasing size; and in general to improve ergonomic qualities.

U.S. Pat. No. 3,931,452 describes an attachment for ceiling-suspended equipment in an operating theater. The stationary ends of girders can be bolted to tracks running in the ceiling, which can also carry cables.

In patent DE 299 03 798 U1, an arrangement is described for moving devices in the clinical area. A powered driver runs along a track mounted on a wall and thus draws a mechanically coupled device, which stands on runner wheels on the floor, from an anesthesiology area, for example, to an operating room.

Patent DE 197 19 349 A1 discloses a medical work area having a mechanically movable projector for projecting images onto a rollable projection surface.

In DE 200 01 134 U1, a surgical system is described having a virtual touch screen, gesture recognition, a video projector and a projection surface. The video projector can be situated on a track device or secured in stationary manner. The video projector and display surfaces can be mechanically movable.

SUMMARY OF THE INVENTION

It is an object of the present invention to make ergonomic improvements possible in a medical treatment facility, in particular in an operating room.

This object is fulfilled by the content of the independent claim.

Refinements are indicated in the dependent claims.

Embodiments of the present invention are based on the idea of configuring an image surface in an operating room or other medical treatment facility so that it is reshapable. The image surface, in particular, is collapsible and/or foldable. If the image surface is configured to be foldable, several areas of the image surface can pivot and/or slide with respect to one another. In a resting condition the image surface, collapsed on itself or folded up, can occupy a markedly smaller area than when it is in an operating condition. Thus the image surface can have large dimensions in the operating condition and small dimensions in the resting condition, so that in resting condition it causes no restricted freedom of movement for medical staff in the operating room.

A display apparatus for displaying medical information in a medical treatment facility includes an image surface to depict information, said image surface being configured so that it can be converted from an operating condition to a resting condition and vice versa.

Medical information is defined for medical staff as relevant information in the form of moving and non-moving images, graph, text, numerals or symbols. The medical treatment facility is, in particular, an operating room. The image surface, in particular, is curved in concave manner in order to improve the immersivity and the evocation of a spatial impression.

As a result of the collapsing and folding of the image surface, areas of the image surface are pushed toward one another. In particular, in operating condition areas of the image surface are alongside one another and in resting condition they are above one another. While the image surface in the operating condition—apart from narrow intermediate spaces or transitional areas in any event—is flat, in the resting condition the image surface is, for example, strongly curved and/or comprises several areas that are positioned essentially parallel to one another and/or are not contiguous areas. At least in one direction, in particular in the vertical direction, the image surface in the resting condition comprises a markedly smaller dimension than in the operating condition. In particular, the dimension in the resting condition is a third or a half smaller than in the operating condition. Other dimensions, in particular dimensions measured in the horizontal direction, can be equal in the resting condition and in the operating condition or can be smaller or larger in the resting position than in the operating condition.

Modification of the image surface by collapsing or folding makes possible a large image surface in the operating condition for large-format depiction of information and a smaller dimension in the resting condition. Owing to the reduced dimension, the image surface in the resting condition can be more easily removed from the area required for unhindered movement of medical staff. In particular, the image surface in the resting condition can be positioned immediately below the ceiling of the medical treatment facility.

In a display apparatus as described here, the image surface is, in particular, a projection surface. A projection surface must comprise predetermined optical properties, while at the same time in many cases meeting only minor mechanical requirements. The projection surface can therefore, on the one hand, have an especially low mass and, on the other hand, be of mechanically flexible configuration. A high mechanical flexibility of the image surface can simplify the reduction of its dimensions by reshaping.

A display device as described here, in which the image surface is a projection surface, can in addition include a projection system for projecting a depiction of information on the projection surface, while the projection system includes a light source, a light modulator and an imaging device such that, in particular, the light source is set apart from the imaging device and/or from the light modulator.

The light source includes, for example, one or more halogen bulbs, high-pressure gas discharge lamps, light-emitting diodes or lasers. In addition, the light source can include one or more mirrors, lenses, filters and other devices to improve the degree of effectiveness of the switching of light of the light source into a transmission beam path and to produce desired spectral properties. The transmission beam path includes, for example, a light conductor cable and/or rod lenses or other lenses or mirrors. The imaging device includes, in particular, a lens or an object lens. The projection system includes, moreover, a light modulator, for example a liquid crystal or LCD component or a digital micro mirror device. The light modulator is, in particular, positioned immediately downstream in the light path from the imaging device. Alternatively, the light modulator can be close to the light source, in particular immediately downstream in the light path from the light source and a collimating device, or at another location between the light source and the imaging device.

The division of the projection system into a light source and an imaging device set apart from the light source can make possible a configuration of the projection system that is optimized with respect to the interference of a vertical laminar flow field in the medical treatment facility.

In a display apparatus with a projection system as described here, the light source can be disposed above a ceiling surface of the medical treatment room and the imaging device below the ceiling surface.

The ceiling surface is the essentially horizontal and essentially level visible underside of the ceiling of the medical treatment room. Because the imaging device is disposed below the ceiling surface, the projection system can project a depiction of information on a projection surface inside the medical treatment room. Because the light source is disposed above the ceiling surface, the construction space required inside the medical treatment room can be reduced. As a result, in particular, the interference of a vertical laminar flow field can be reduced. In addition, owing to the placement of the light source above the ceiling surface, heat effluents of the light source can be generated and diverted outside of the medical treatment room.

Alternatively, in a display apparatus with a projection system as described here, the light source and imaging device are disposed at a distance from one another inside the medical treatment room. In particular, below the ceiling surface the imaging device is disposed in the center or essentially in the center of a vertical laminar flow field and the light source is disposed outside the vertical laminar flow field and the two are coupled, for example, by a light conductor cable to transmit the light generated by the light source. The light conductor cable can have a small cross-section and therefore cause only a minor interference in the vertical laminar flow field.

In a display apparatus as described here, the image surface can be configured as an image screen.

In particular, the image surface is the controllable light-emitting surface of an organic light emitting diode (OLED) display. OLED displays can also be generated in curved shape, in particular with positive Gaussian curvature or dome-shaped curvature. At the same time, OLED displays can have a small thickness and thus also a low mass and a high mechanical flexibility. Because of a dome-shaped curvature, the immersivity can be improved and a three-dimensional image impression can be generated. Because of the flexibility, reshaping is possible between the operating condition and the resting condition.

In a display apparatus as described here, the image surface, in particular, comprises several areas, which in operating condition form an image surface and which in a resting condition are disposed at a distance from one another.

To form the image surface, the areas of the image surface in operating condition are disposed alongside one another and flush, so that their edges border on one another or leave only small distances that do not stand out or disturb in the expected observation distance. In resting condition the areas of the image surface, in particular, are not disposed alongside one another but rather on top of one another, so that in each case a good number of the surface normals of one area penetrate or intersect at least one other area. At least a few edges of areas that in operating condition border, or almost border, on edges of neighboring areas have, in resting condition, a great distance from all edges of all other areas. In other words, the areas in operating condition are disposed close to one another and the areas in resting condition are, in particular, stacked on top of one another. The transformation of the image surface between the operating condition and the resting condition includes in particular a sliding motion of the areas in relation to one another, such that the areas of the image surface can be pivoted simultaneously in relation to one another.

An image surface made up of several areas that are slid in relation to one another in the reshaping from operating condition to resting condition makes possible a compact resting condition in which the image surface, in particular, can be stowed in a relatively small container. Simultaneously the individual areas of the image surface can be rigid, so that the number of technologies used for generating an image on the image surface is increased.

A display apparatus as described here includes in particular a foldable structural device and an elastic membrane that is held by the structural device.

The foldable structural device includes, in particular, rigid or elastic, straight or curved rods and/or blades that are mechanically coupled with one another by joints. The surface of the elastic membrane forms, in particular, the aforementioned projection surface. The foldable structural device and the membrane are, for example, configured in similar manner to a carriage roof (arched scissors between two joints) or to an umbrella or parasol or to a domed tent.

A foldable structural device with an elastic membrane held by the foldable structural device can have an especially low mass and can be folded compactly. At the same time the image surface formed by the elastic membrane can achieve an at least approximately spherical shape.

With a display apparatus as described here, having a foldable structural device and an elastic membrane held by the foldable structural device, the elastic membrane can be removed from the foldable structure and sterilized separately.

For example, the elastic membrane can be connectable with the foldable structural device by means of push-buttons, Velcro® fasteners or pockets to receive ends of blades of the foldable structural device, and can be removable from it again without destruction and in particular without use of a tool. The elastic membrane, in particular, is autoclavable. If the elastic membrane is an OLED display, it can, in particular, be cold-sterilized.

The elastic membrane's removable and sterilizable qualities can reduce operating costs for the display apparatus, in particular costs for cleaning and sterilization.

With a display apparatus as described here, the image surface can be curved in one or in two directions.

In particular, the image surface has a dome-shaped curvature or comprises a positive Gaussian curvature. For example, the image surface has the shape of a portion of a surface of a cylinder, sphere, or other biaxial or tri-axial ellipsoid.

Because of a concave curvature of the image surface, immersivity can be increased and a three-dimensional image impression can be achieved. From these viewpoints, for purposes of observing an image recorded by an endoscope with a viewing angle of 70 degrees, for example, an image surface in the shape of a portion of a spherical surface can be advantageous when the image displayed on the image surface is observed on the same spherical surface from a site opposite the image surface.

A display apparatus as described here can, in addition, include a rectification device to reshape an image that is to be displayed by the image surface in such a way that the image is perceived by an observer at a predetermined site as non-distorted.

In particular, a depiction of an image on a curved image surface can be perceived by an observer as distorted even when the observer's position is centered in front of the image surface. This applies as well to a depiction of an image on a flat surface when the observer is not situated at the center in front of the image surface. In particular, an observer perceives an image in which parallel straight lines appear not to be straight and/or not parallel and right angles do not appear as right angles. This distorted perception can be prevented or corrected by a corresponding reshaping of the image depicted on the image surface.

In the case of a projection of an image on a projection surface, the rectification device can include optical devices, for example a projector with a corresponding corrective imaging device that is also adapted to the shape of the image surface (in particular, object lens, lenses, or mirror system). Alternatively or in addition, the rectification device can include an image processor that modifies an image signal that controls the depiction of the image on the image surface.

A display apparatus as described here can, in addition, include a rectification device with an input for receiving a signal that is dependent on a position of an observer, in such a way that the rectification device is configured to control the display apparatus depending on the observer's position.

If the observer of the image surface is not situated precisely in the center with respect to it and/or is not precisely centered with respect to an image surface configured as a projection surface in the case of a curvature of the image surface and/or possibly a positioning of a project, an image impression can arise that is distorted or unnatural-seeming for the observer. To control the display apparatus to rectify the image perceived by the observer, the image signal used to generate the image on the image surface can be modified accordingly. If the image surface is a projection surface and the display apparatus in addition includes a projection system with a light modulator and an imaging device, then alternatively or in addition the image can be rectified by pivoting and sliding the light modulator and imaging device or parts of the imaging device.

The control of the rectification device depending on a signal that indicates the position of the observer makes it possible to depict on the image surface an image that is perceived by the observer as undistorted, largely independently of his own standpoint in relation to the image surface.

A display apparatus as described here can, in addition, include a container that is configured to enclose the image surface in a resting position.

In particular, the container is configured to incorporate the image surface in its resting condition with reduced dimensions. The container can protect the image surface in its resting condition and promote a quieter and/or more orderly overall impression of the medical treatment room and thus improve the ergonometric conditions.

With a display apparatus with a container as described here, the container can be movably attached to a track on a ceiling surface of a medical treatment room.

In particular, the container is mounted to several parallel tracks, or essentially parallel tracks, and can be moved or slid along a path determined by said tracks.

The mounting of the container on the ceiling supply system can make possible a short path between the resting position of the image surface in the container and an operating position. In addition, the container, in the framework of a related functioning of the ceiling supply system, can be movable with the image surface in the horizontal direction in order to make the image surface available at various locations in the medical treatment facility.

A display apparatus with a container on a ceiling supply system as described here can also include a power drive device to move the image surface between the resting position inside the container and an operating position in which information can be depicted visibly for medical staff on the image surface.

The power drive device includes in particular an electrical motor, a pneumatic or hydraulic motor, a gas pressure or other spring or a combination of these. In particular, a gas pressure or other spring can partly or completely compensate the speed of the device that constitutes the image surface so that the manual or mechanical movement of the screen between the resting position and the operating position requires only a force that is markedly smaller than the weight of the device that constitutes the image surface. In particular, a power drive device that can be powered by signals of a control device can make possible a rapid, precise and comfortable movement of the image surface between the resting position and the operating position.

A display apparatus with a power drive device as described here can also include a device to record a gesture by medical staff and to control the power drive device depending on the recorded gesture.

The device to record a gesture comprises in particular a time-of-flight camera, a stereo camera or other video camera, an ultra-sound sensor or other sensor by means of which a hand or other body part of the medical staff can be recorded. In addition, the device is configured to record the movement of the hand or other body part and to identify it with a gesture that is associated with a control command.

The device to record a gesture makes possible a contact-free and, when specially configured for it, intuitive operation of the display apparatus. It can become easier therefore for medical staff to bring the image surface quickly into its resting position or into its operating position in order to optimize the treatment space ergonomically depending on the situation.

With a display apparatus as described here, the image surface is in particular a projection surface that can move along a path determined by a track device, while the display apparatus in addition includes a projector that can be slid along the path to project a depiction of information onto the projection surface and a positioning device to establish the position of the projector and of the projection surface on the path, so that the positioning device is configured to position the projector and projection surface on positions essentially opposite one another on the path determined by the track device.

The positioning device includes in particular a mechanical coupling. For example, a rope runs along the path determined by the track device, so that both the projection surface and the projector are coupled with the rope at locations distanced from one another. Alternatively, the positioning device includes, for example, a control device to control the positioning of the projector and projection surface, in particular by power drive devices as described hereinafter.

The projector and projection surface are disposed in essentially opposite positions on the path determined by the track device when the angle (based on the center point of the surface circumscribed by the predetermined path) between the center point of the light outlet surface of the projector and the center point of the projection surface is at least 120 degrees. The projector and projection surface are, in addition, disposed on essentially opposite positions on the path determined by the track device when the distance, measured along the predetermined path, between points corresponding to one another on a trolley device of the projector and on a trolley device of the projection surface make up at least one-third of the entire length of the predetermined path. The projector and projection surface, in addition, are disposed on essentially opposite positions on the path determined by the track device when the distance of the straight lines through the center point of the light outlet surface of the projector and the center point of the projection surface from the surface normal to the center point of the surface circumscribed by the predetermined path corresponds to a maximum of one-fourth of the sum of the distances of the two center points of the light outlet surface of the projector and projection surface from the surface normal.

A display apparatus as described here can also include a power drive device to mechanically move the image surface along the path determined by the track device. If the carrier system bears a display apparatus in the shape of a projector and a projection surface, one power drive apparatus, in particular, is provided in each case to move the projector and the projection surface along the predetermined path.

With a display apparatus as described here, with a projection surface and a projector, the positioning device includes, in particular, a control device and at least either a first power drive device to move the projector along the path determined by the track device or a second power drive device to move the projection surface along the path determined by the track device, so that the control device comprises a control output to control at least either the first power drive device or the second power drive device.

Additional power drive devices can be provided to lift and pivot the projector and/or the projection surface in one or two directions each.

The power drive device or devices can make possible a self-actuating or automatic positioning of the display apparatus or of its components or a positioning, controlled for example by gestures, that requires no touching of the display apparatus or of its component.

A display apparatus with a power drive device to mechanically move the display apparatus or a component of the display apparatus as described here can in addition include a device to record a position or gesture of medical staff and to control the power drive device depending on the recorded position or gesture.

The recording device includes, in particular, a time-of-flight camera, a stereo camera or one or more other cameras for two-dimensional or three-dimensional recording of a room area, where the room area in particular includes the surgical site, the operating table and/or its surroundings. The recording device also includes an image recognition or pattern recognition apparatus to identify medical staff or the head or a hand or other body part of medical staff.

A device to record a position or a gesture can make possible self-actuating or automatic adjustment of the positions of the display apparatus or of the projector and projection surface at the momentary location of the relevant medical staff and at the momentary viewing angle. In addition, the positions of other persons and of equipment can be taken into account in order to prevent shadowing or partial covering of the display apparatus and to ensure unrestricted legibility. Recording of gestures can make possible a simple and intuitive control of the carrier system. Medical staff can thereby be relieved and concentrate to a greater extent on its actual medical tasks.

With a display apparatus as described here, which includes a positioning device with a control and at least one power drive device, the control device in particular comprises an input for receiving a position signal that is dependent on the position of the projection surface in relation to the projector or on the absolute positions of projection surface and projector.

As an alternative to recording of absolute or relative positions of projectors and of the projection surface, the power drive devices can comprise stepper motors, such that the positions can be determined by counting or registering completed steps.

BRIEF DESCRIPTION OF THE DRAWINGS

Embodiments are described in closer detail hereinafter with reference to the appended drawings, which are as follows.

FIG. 4 shows a schematic sectional depiction of a track device.

FIG. 5 shows a schematic sectional depiction of an additional track device.

FIG. 6 shows a schematic sectional depiction of an additional track device.

FIG. 7 shows a schematic sectional depiction of an additional track device.

DETAILED DESCRIPTION OF THE INVENTION

Figure 1:
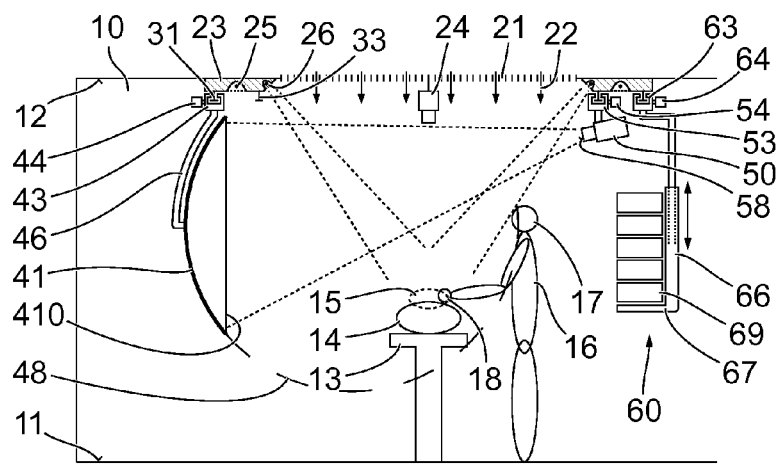
FIG. 1 shows a schematic depiction of a medical treatment facility.

FIG. 1 shows a schematic depiction of a medical treatment facility 10, in particular of an operating room, having a floor surface 11 and a ceiling surface 12. The plane of projection of FIG. 1 is perpendicular to the floor surface 11 and to the ceiling surface 12. The ceiling surface 12, in particular, is level or essentially level and is formed by the underside of the ceiling that is visible from the interior of the medical treatment facility 10. On the floor surface 11 of the medical treatment facility 10 there stands or is affixed a treatment table 13, on which a patient 14 can lie, for example during a surgical procedure. A broken line indicates the outline of a surgical site 15. Alongside the treatment table 13 stands a physician or other medical staff 16 with a head 17. The medical staff 16 holds one hand 18 in the surgical site 15.

In a central area above the treatment table 13, numerous air nozzles 21 are mounted on the ceiling surface 12. The air nozzles 21 are configured, for example, by openings in grids. The air nozzles 21 are configured to generate a vertical laminar flow field 22 of low-dust, low-germ, tempered air, where the low-dust and low-germ air is furnished by a ventilating system that is not shown in the drawings. The area of the ceiling surface 12 occupied by the air nozzles 21 can be, for example, circular, elliptical, square or rectangular and can comprise a total surface of several square meters.

Vertically above the treatment table 13 and the surgical site 15, a room video camera 24 is situated below the ceiling surface 12, in particular immediately below the ceiling surface 12. Contrary to the depiction in FIG. 1, the room camera 24 can be positioned in the ceiling of the medical treatment facility in such a way that only a light inlet surface of the room camera 24 is positioned at the height of the ceiling surface or immediately below it. The room camera 24 can constitute a disturbance of the flow field 22 generated by the air nozzles 21 and is therefore configured as small as possible, in particular, and/or as free-flowing as possible.

The room camera 24 is intended to record the surgical site 15 or to record a larger area that can include the entire treatment table 13 and any medical staff 16 present at the treatment table 13. The room camera 24 can be a time-of-flight camera or a stereo video camera for three-dimensional recording of the surgical site 15 or of a greater area. Instead of a room camera 24 or in addition thereto, several video cameras with different viewing angles and/or with different functions can be provided, for example a time-of-flight camera and a two-dimensional high-resolution camera without recording a third dimension.

The area occupied by the air nozzles 21 on the ceiling surface 12 is surrounded by a ceiling supply system that is, in particular, circular in shape, or a component 23 of a ceiling supply system. Integrated in the ceiling supply system 23 are, in particular, a general illumination 25 for essentially homogeneous illumination of the entire medical treatment facility or of a central area of the medical treatment facility 10 and a surgical light 26 for illuminating the surgical site 15. The surgical light 26 includes, in particular, a number of single emitters, which each generate narrow light cones, and which can be adjustable and/or controllable individually or in groups with respect to the direction of the light emission and/or the intensity or generated light flow and/or with respect to the size of the particular illuminated angle area and/or with respect to the direction of the light emission. In addition, tracks 31, 33 are integrated in the ceiling supply system 23 that each likewise surround in circular shape the area of the ceiling surface 12 occupied by the air nozzles 21. Contrary to the depiction in FIG. 1, the ceiling supply system 23 can be partly or completely integrated in the ceiling of the medical treatment facility 10, so that the underside of the ceiling supply system 23 is shaped flush with the ceiling surface 12.

Several devices, apparatuses or systems are each affixed to one of the tracks 31, 33 or hanging on one of the tracks 31, 33 and can be moved or slid manually or mechanically along the paths parallel to the ceiling surface 12 that are determined by the tracks 31, 33. A few examples are presented hereinafter with reference to FIG. 1 and the other drawings.

One trolley 43 is mounted on the first track 31 of the ceiling supply system 23 and carries a projection surface 41 via a carrier 46. A power drive device 44 is provided on the trolley 43 for electro-mechanical movement of the trolley 43 and, with it, of the carrier 46 and projection surface 41 along the path determined by the first track 31. The projection surface 41 has, in particular, the shape of a portion of a spherical surface or of a surface of a two- or three-axis ellipsoid. The border 410 of the projection surface 41 lies, for example, in a plane and is circular or essentially circular in shape or has the shape of a line of intersection of a cylindrical mantle with a spherical surface, so that the cylinder in particular comprises an essentially rectangular cross-section with rounded corners.

The projection surface 41 is formed by a surface, facing the medical staff 16, of a corresponding body, which for instance is spherical-shell-shaped and whose structural characteristics are not described in further detail here.

An additional trolley 53 can move along the path determined by the second track 33 and carries a projector or a projection system 50 for projecting a moving or non-moving image, a graph, text, figures, symbols and other images of information on the projection surface 41. The projector 50 comprises traits and characteristics, in particular, that with respect to the projection of light are conventionally associated with a video beamer. A power drive device 54 on the other trolley 53 makes possible a mechanical movement of the other trolley 53 and of the projector 50 along the path determined by the second track 33.

The projector 50 and the projection surface 41 together form a display device for displaying medically relevant information for medical staff 16. In addition to the power drive devices 44, 54 on the trolleys 43, 53, other power drive devices can be provided on the projection surface 41 and/or on the projector 50 in order to be able to pivot these in each case in one or more directions, in particular in the horizontal and vertical directions. As a result, the projection surface can be directed at all times at the medical staff 16 and/or at the projector 50 and the projector 50 can be directed at all times at the projection surface 41.

Another trolley 63 on the first track 31 carries a carrier apparatus 60 for one or more medical devices 69. The other trolley 63 and with it the carrier apparatus 60 can be moved along the path determined by the first track 31 by means of a power drive device 64 on the other trolley 63. The carrier apparatus 60 includes a device holder 67 and a vertical blade 66 that connects the device holder 67 with the trolley 63 and can be offset at an angle in the upper area, as shown in FIG. 1. The vertical blade 66 in the example shown in FIG. 1 is telescopable and thus forms a vertical steering device for the device holder 67 and the medical devices 69 that are held by the device holder 67 and that make possible a vertical movement of the device holder 67 and medical devices 69 as indicated by a double arrow.

The device holder 67 in the example shown in FIG. 1 is configured as an essentially horizontal carrier plate on which the medical device or devices 69 stand. One or more power drive devices, not shown in FIG. 1, can be provided and configured to rotate the device holder 67 or the entire carrier apparatus 60 around a vertical axis and/or to move the device holder 67 in the vertical direction.

In addition to the power drive devices 43, 53, 63, shown or not shown in FIG. 1 and described above, or partly or completely integrated in them, position sensors can be provided to record the position of the trolleys 43, 53, 63 along the path determined by the tracks 31, 33, angle positions and positions in vertical direction of the projection surface 41, of the projector 50 and/or of the device holder 67. These sensors can be coupled with a steering device, described below with reference to FIG. 28. Provided that stepper motors are used in the power drive devices, the corresponding positions or coordinates can be determined alternatively by counting the completed steps.

The steering device presented below with respect to FIG. 28 can guide the power drive devices on the basis of the recorded positions and optionally in addition on the basis of the position or positions of relevant medical staff or on the basis of gestures of the medical staff recorded by the room camera 24 or other sensors. The steering device can thus provide at all times an arrangement and alignment, which are optimal for medical staff from the ergonometric viewpoint, of the projection surface 41 and of the medical devices 69 carried by the carrier apparatus 60. By dispensing predominantly or—as indicated in FIG. 1—completely with conventional ceiling arms, a vertical laminar flow field 22 becomes possible that is largely or completely free of failures.

Figure 2:
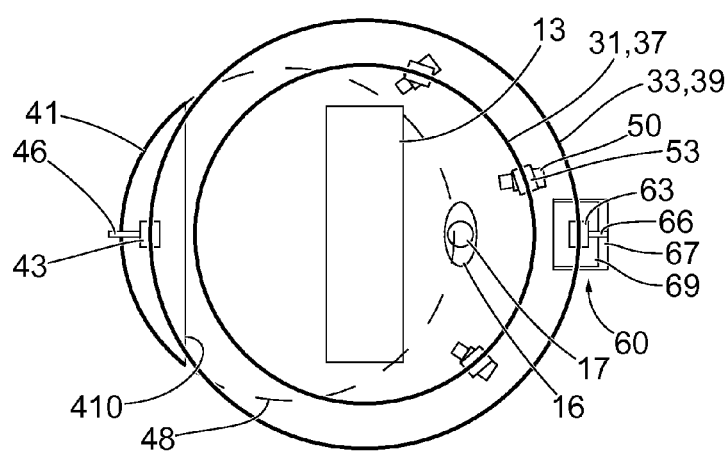
FIG. 2 shows an additional schematic depiction of the medical treatment facility from FIG. 1.

FIG. 2 shows another schematic depiction of the medical treatment facility from FIG. 1. The plane of projection of FIG. 2 is perpendicular to the plane of projection of FIG. 1 and parallel to the floor surface 11 and to the ceiling surface 12 of the medical treatment facility 10. The tracks 31, 33 and the paths 37, 39 determined by the tracks 31, 33 circumscribe in circular manner the area of the ceiling surface that is positioned above the treatment table 13. The trolley 43 along with the projection surface 41, the trolley 53 along with the projector 50, and the trolley 63 along with the carrier apparatus 60 can be moved along the paths 37, 39 determined by the tracks 31, 33. The projection surface 41 and the carrier apparatus 60 are shown in FIG. 2 in the same position as in FIG. 1; the projector 50 is shown in a position that is slightly displaced with respect to the position shown in FIG. 1.

In FIGS. 1 and 2, the contours of the spherical surface on which the projection surface 41 is situated are indicated in broken lines. In the situation illustrated in FIGS. 1 and 2, the head 17 and/or the eyes of the medical staff 16 are approximately on this spherical surface 48. This configuration has shown itself, for example in observing images that are recorded by an endoscope with an image angle of 70 degrees, to be approximately optimal with respect to achieving an immersive, three-dimensional image impression for the medical staff 16.

Contrary to FIG. 1, in FIG. 2 one also sees additional projectors, not labeled with reference numbers, that can be operated in alternation or simultaneously to allow a uniform illumination of the projection surface 41.

Figure 3:
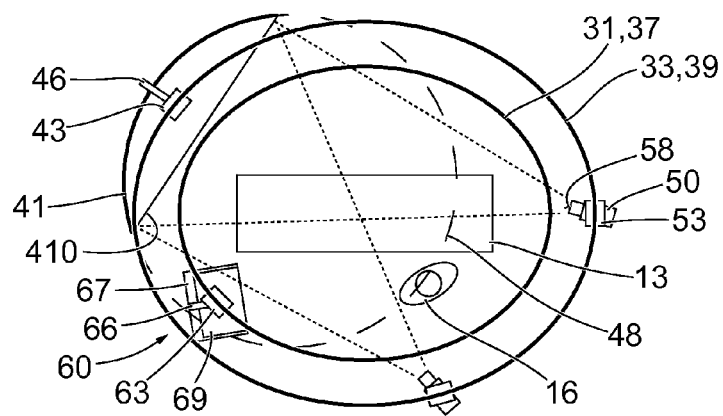
FIG. 3 shows a schematic depiction of an additional medical treatment facility.

FIG. 3 shows a schematic depiction of an additional medical treatment facility, which resembles in some respects the medical treatment space described above with reference to FIGS. 1 and 2. Contrary to the example in FIGS. 1 and 2, in the example in FIG. 3 the tracks 31, 33 and the paths 37, 39 determined by the tracks 31, 33 each have an elliptical shape. An elliptical or oval shape of the paths 37, 39 can be advantageous, for example, under tight space conditions. In the configuration shown in FIG. 3, both the projection devices 50 and the projection screen 41 and carrier apparatus 60 are each rotated with respect to the associated trolleys 53, 43 or 63.

FIGS. 4 through 9 show schematic depictions of various embodiments of ceiling supply systems 23 and in particular of the track devices formed by tracks 31, 32, 33, 34 on the ceiling supply systems 23, as well as of trolleys 43, 53 on the tracks 31, 32, 33, 34. The illustrations each have for the most part the quality of cut-out depictions, where the planes of projection or the illustrated sectional planes correspond to the plane of projection of FIG. 1 and thus are disposed vertically in the medical treatment facility.

In FIGS. 4 through 9, a room illumination 25 is shown in each case, with a light source and an indicated reflector. Structural details of the ceiling supply systems 23 and of the trolleys 43, 53 are each indicated in all cases. Also, the ceiling of the medical treatment space in FIGS. 4 through 9 is indicated in each case only by the ceiling surface 12 and the air nozzles 21 to generate the vertical laminar flow field 22.

Some of the embodiments presented with reference to FIGS. 4 through 9, alternatively, can be integrated in the ceiling of the medical treatment facility provided that the underside of the supply system 23 or the undersides of the tracks 31, 32, 33, 34 are positioned flush with the ceiling surface.

In the example illustrated in FIG. 4, tracks 31, 33 are foreseen, with one trolley 43 situated on each. The tracks 31, 33 can be situated parallel or essentially parallel to one another, or can be at a constant distance. Alternatively, the tracks 31, 33 can be at a varying distance. Each of the two tracks 31, 33 has a cross-section that corresponds essentially to a "T" rotated by 180 degrees. Each trolley 43 comprises several rollers 430 whose axles are each perpendicular or essentially perpendicular to the local direction of the path 37 or 39 (see FIGS. 2, 3) determined by the track 31 or 33. In each case one or more rollers 430 are positioned over a horizontal running surface on the track 31, 33 that is aligned upward in order to transmit the weight impact of the trolley 43 and the devices affixed to it onto the track 31, 33. In each case one or more rollers 430 are contiguous with lateral or vertical running surfaces or with horizontal running surfaces of the tracks 31, 33 that are aligned downward in order to divert horizontal forces, forces aligned vertically upward, and tipping moments onto the tracks 31, 33. One or more running wheels 430 in each case can be powered by a power drive device 44 in order to move or slide the trolley 43 along the corresponding track 31, 33.

In addition, a contact track 29 of an electrically conductive material is provided parallel to each track 31, 33. A sliding contact 439 is positioned on the trolley 43 in such a way that it is contiguous with the contact track 29 and forms an electrically conductive connection with it. A spiral spring or other elastic element can be provided in order to press the sliding contact 439 against the contact track 29. The sliding contact 439 thus forms a contact device to form an electrically conductive contact with the contact track 29. The contact track 29 and the sliding contact 439 can be provided to transmit electric current and electric signals between the ceiling supply system 23 and the trolley 43. The second pole, required to close a power circuit, is formed for example by the tracks 31, 33. Alternatively or additionally, further contact tracks can be provided, with which other sliding contacts are contiguous.

Besides electric power, it is possible to transmit, in particular, low-frequency signals or signals with low data rates or bandwidths over the contact tracks 29 and the sliding contacts 439. In particular, control signals for the power drive device 44 and, in the opposite direction, position signals, which indicate positions in the corresponding degrees of freedom, are transmitted by means of the contact tracks 29 and the sliding contacts 439. At least when the trolley 43 is not moved, it is possible in addition to transmit signals with higher data rates or bandwidths, for example image signals.

FIG. 5 shows a schematic depiction of an embodiment that in a few respects resembles the embodiment in FIG. 4. In the embodiment in FIG. 5, the trolley 43 engages in two opposite U-shaped tracks 31, 33 that are turned away from one another and is guided therein with several rollers 430 in each case. The trolley 43 here also grips two diaphragms 28. The diaphragms 28 cover two tracks 31, 33 partly or completely, so that these are not visible to an observer in the medical treatment facility. In addition, the diaphragms 28 can protect the tracks 31, 32 and the rollers 430 on the trolley 43 from contamination and damage and can absorb or repress friction occurring on the tracks 31, 32 and on the rollers 430.

Contrary to FIGS. 4 and 6 through 9, examples of simple structural characteristics of the ceiling supply system are also indicated in FIG. 5. The tracks 31, 32 are components of a profile module that can first be anchored on the ceiling surface 12. Thereafter, the room illumination 25 and the diaphragms 28 in particular can be inserted as a unit into the profile module.

Contact tracks and sliding contacts as in the example in FIG. 4 are not shown in FIG. 5 but can also be provided in the embodiment in FIG. 5.

FIG. 6 shows a schematic depiction of an additional embodiment, in which the trolley 43 is guided and held by two tracks 31, 32. Each track 31, 32 comprises a C-shaped cross-section that is open on the underside. Rollers 430 of the trolley 43 are positioned inside the C-shaped cross-sections of the tracks 31, 32 and support themselves there on horizontal or essentially horizontal running surfaces. To guide the trolley 43 in the horizontal direction perpendicular to the paths determined by the tracks 31, 32, the guide studs 311, 321, for example, which are indicated in FIG. 6 and protrude upward on the edges of a track 31, 32 that are opposite one another, are provided for the rollers 430. As an alternative or in addition, other rollers can be foreseen that are contiguous with the vertical running surfaces in the tracks 31, 32 in order to transmit horizontal forces onto the tracks 31, 32.

In the hollow spaces in the tracks 31, 32 that are open underneath, one or—as indicated in FIG. 6—more contact tracks 29 are positioned in each case. Corresponding sliding contacts 439 are provided on the trolley 43.

FIG. 7 shows a schematic depiction of an additional embodiment in which two parallel tracks 31, 32 are positioned on sides of the ceiling supply system 23 that face away from one another. Each of the tracks 31, 32 protrudes horizontally in a stud-shaped manner. The trolley 43 comprises rollers 430 that are contiguous with running surfaces that are horizontal and directed upward, or vertical, or horizontal and directed downward and that make possible a diversion or transmission of forces and moments onto the tracks 31, 32.

Figure 8:
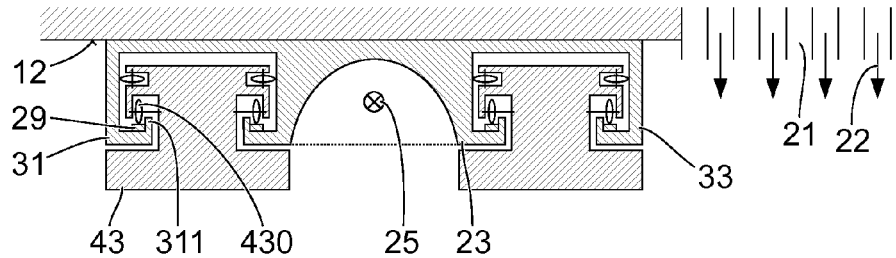
FIG. 8 shows a schematic sectional depiction of an additional track device.

FIG. 8 shows a schematic depiction of an embodiment in which, similarly as in the embodiment in FIG. 4, two trolleys 43 independently of one another are each guided and held by a track 31, 33. The individual tracks 31, 33 and the guidance of the trolleys 43 in the tracks 31, 33 resemble the embodiment in FIG. 6. Contrary to the embodiment in FIG. 6, in the embodiment in FIG. 8, alternatively to the guide studs 311 or—as shown in FIG. 8—in addition to them, rollers 430 are provided that are contiguous with vertical running surfaces in the tracks 31, 33. In addition, contact tracks 29 are provided in the tracks 31, 33 that form running surfaces for one or more guide wheels 430 in each case. Transmission of electric power and/or electric signals to or from the trolley devices 43 is possible via rollers 430 that are contiguous with the contact tracks 29.

Figure 9:
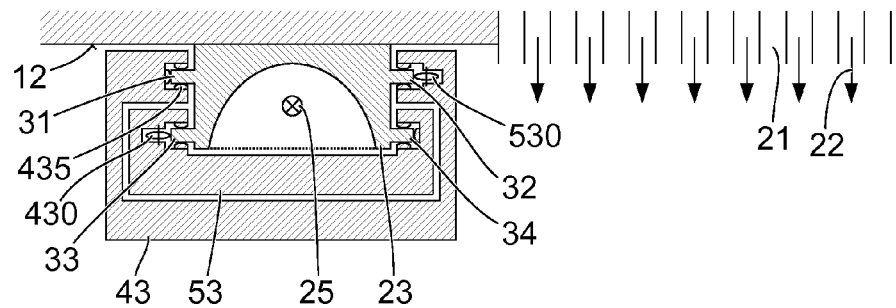
FIG. 9 shows a schematic sectional depiction of an additional track device.

FIG. 9 shows a schematic depiction of an additional embodiment in which, similarly as in the embodiment in FIG. 7, horizontally protruding stud-shaped tracks 31, 32, 33, 34 are provided on sides of the ceiling supply system 23 that are turned away from one another. Contrary to the embodiment in FIG. 7, two pairs of tracks 31, 32 or 33, 34 are provided. A first trolley 43 is held and guided by a first pair of tracks 31, 32. A second trolley 53 is held and guided by a second pair of tracks 33, 34. Owing to a corresponding configuration of the trolleys 43, 53, as is indicated by way of example in FIG. 9, the trolleys 43, 53 can be moved independently of one another along the paths determined by the tracks 31, 32 or 33, 34 without colliding with one another.

Contrary to the embodiments in FIGS. 4 through 8, in the embodiment in FIG. 9, instead of rollers 430, glider bearings 435 are predominantly provided. In addition to the glider bearings, in each case a roller 430, 530 is provided that can be powered by a power drive device, not shown in FIG. 9, in order to move the associated trolley 43, 53.

In the embodiments in FIGS. 4 through 8, the rollers 430 can be partly or completely replaced by glider bearings 435, as described above with reference to FIG. 9. In the embodiment in FIG. 9, the glider bearings 435 can be partly or completely replaced by rollers. In particular, in each of the embodiments presented with reference to FIGS. 4 through 9, it is possible to provide rollers to absorb weight impacts, and glider bearings for horizontal guidance and to absorb other forces and moments. It can be advantageous in each case to provide a powered running wheel to move the trolley. To make possible a power drive without slippage, a power-drive running wheel can be configured as a toothed wheel and an opposite running surface as a gear rack. Alternatively to a form-locked or force-locked roller acting reciprocally with the associated running surface, it is also possible to use an electromagnetic linear drive, an ultrasound motor, a drive via rope pull or manual mobility.

The rollers or glider bearings of the embodiments in FIGS. 4 through 9 can be replaced partly or completely by devices for magnetic hoisting and guidance of the trolleys 43. For this purpose, permanent magnets and/or electromagnets and devices for controlling constant distances are provided. Devices for magnetic hoisting and guidance of the trolleys 43 can, in addition, be configured to power the trolleys magnetically.

In FIGS. 4 through 9, reference number 43 has been used by way of example for the trolleys, and in FIG. 9 reference number 53 is also used. Reference numbers 43, 53 refer in FIGS. 1 through 3 to the trolleys that are associated with projection surfaces 41 or projectors 50. The trolleys shown in FIGS. 4 through 9, however, can also be associated with the carrier apparatus 60 from FIGS. 1 through 3 or can carry other devices, in particular also the devices presented hereinafter with reference to FIGS. 10 through 24.

Figure 10:
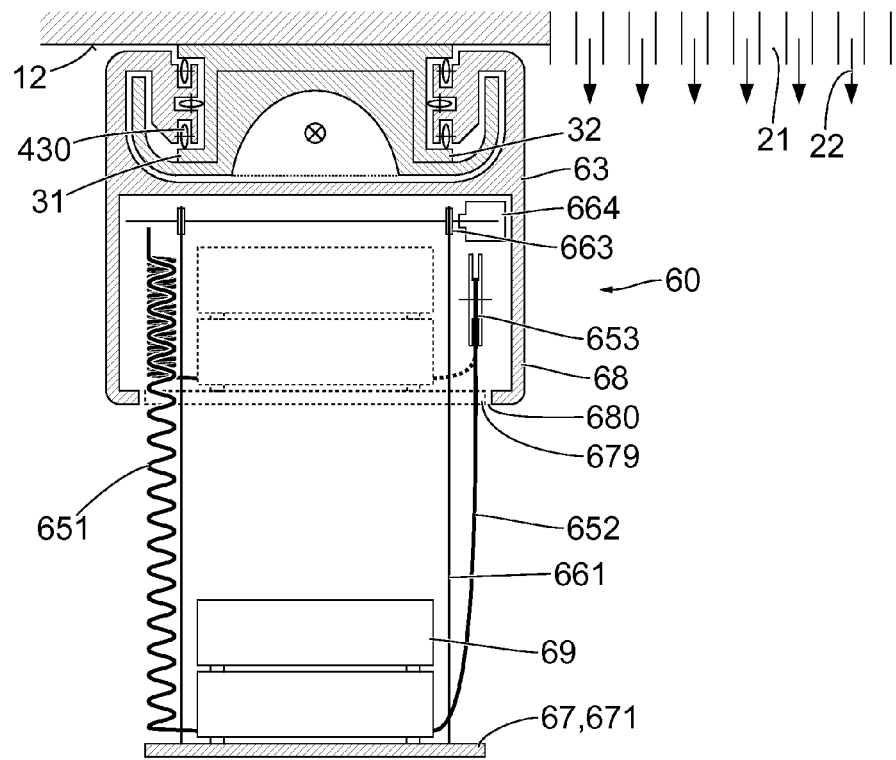
FIG. 10 shows a schematic depiction of a carrier apparatus.

FIG. 10 shows a schematic depiction of an additional carrier apparatus 60 with a configuration that is an alternative to the one shown in FIGS. 1 through 3. The depiction in FIG. 10 has to some extent the character of a sectional depiction, such that the plane of projection corresponds to those in FIGS. 1 and 4 through 9.

The trolley 63 is connected with a container 68 or—as indicated in FIG. 10—is of one-piece configuration. There is an opening 680 on the underside of the container 68. The device holder 67 in this embodiment is not guided on a vertical telescopable blade, but rather suspended on several ropes 661, whose upper ends can be wound up on reels 663. The reels 663 can be powered by an electromotor 664 in order to wind or unwind the ropes 661 and thus to move the device holder 67 vertically upward or downward. Thus the ropes 661, the reels 662 and the electromotor 664 form a lifting device for the device holder 67.

The device holder 67 is depicted with two medical devices 69 in a lower position or operating position 671 in broken lines in FIG. 10. The device holder 67, in addition, is depicted together with the medical devices 69 in broken lines in a higher resting position 679. In the resting position 679 the device holder 67 closes the opening 680 on the underside of the container 68. The devices 69 are positioned in the hollow space configured by the container 68 and there largely protected from contamination and damage. Owing to an optically quiet configuration of the outside of the container 68 and of the underside of the device holder 67, a calm optical impression emerges that is not likely to distract medical staff from their task and that can enhance concentration on relevant information sources.

Many medical devices 69 are dependent on a supply of electrical power, illuminating light from a high-voltage light source, compressed air or other fluids, as well as on an exchange of electrical or optical signals (for example via a Storz Communication Bus SCB) with other devices. To make possible a start-up and turn-off of the devices 69 without previous establishment or interruption of current connections, the medical devices 69 can remain constantly connected with power, signal, light and fluid sources, both in the operating position 671 and in the resting position 679 and in all positions in between.

For this purpose, as an alternative or simultaneously, one or more extensible cables 651 and/or one or more coilable cables 652 are provided between the interior of the container 68 and the device holder 67 or the medical devices 69 positioned on the device holder 67. The extensible cable 651 has, in particular, a helical shape, similar to a cable generally called a spiral cable, as is provided conventionally between a telephone and the user. The coilable cable 652 can be rolled up on a reel 653. The reel 653 can be powered mechanically or by a spring in order to roll up the coilable cable 652 by self-actuation when the device holder 67 with the medical devices 69 is raised from the operating position 671 into the resting position 679.

Figure 11:
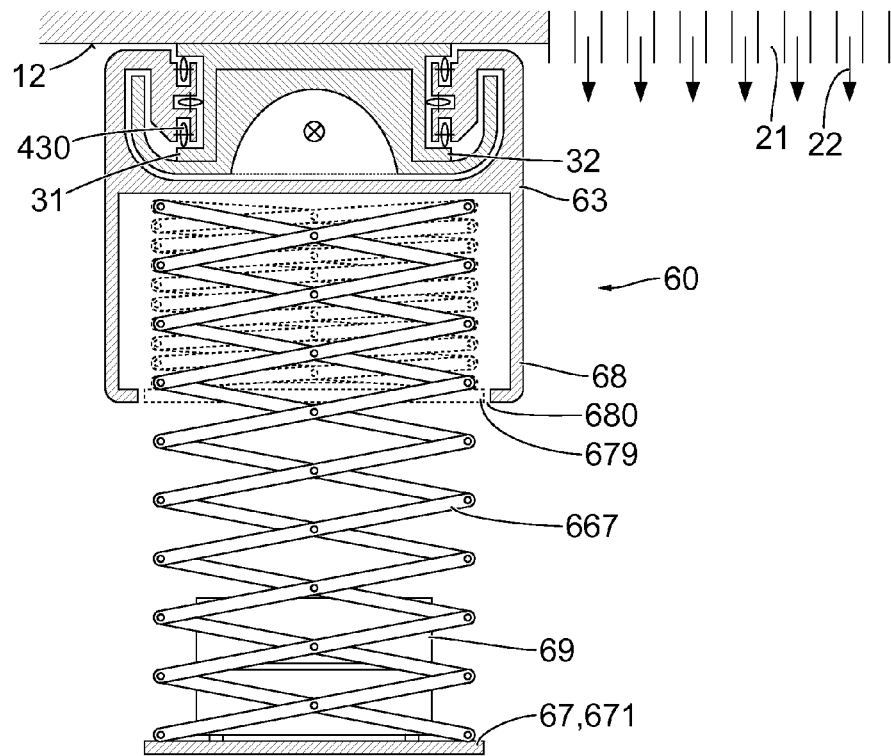
FIG. 11 shows a schematic depiction of an additional carrier apparatus.

FIG. 11 shows a schematic depiction of an embodiment of a carrier apparatus 60 that is an alternative to the embodiment in FIG. 10. The embodiment shown in FIG. 11 resembles the embodiment presented above with reference to FIG. 10 in a few characteristics. What particularly distinguishes the embodiment in FIG. 11 from the one in FIG. 10 is that instead of several ropes 661, a scissors mechanism 667 is provided. The scissors mechanism 667, contrary to the cables of the embodiment in FIG. 10, makes possible a rigid guidance of the device holder 67, aside from the residual elasticity that is proper to it. The device holder 67 is not only kept at all times in the horizontal position by the scissors mechanism—as also by the cables of the embodiment in FIG. 10. The scissors mechanism 667, in addition, can also transmit onto the trolley 63 the horizontal forces exerted on the device holder 67. Thus the scissors mechanism 667 has the function of a steering device for largely rigid guidance along a predetermined straight vertical course.

In addition, the scissors mechanism 667 can be used to move the device holder 67. A force that, for example, impacts only on the topmost pair of blades of the scissors mechanism 667 leads to a uniform reshaping of the entire scissors mechanism 667. To that extent, the scissors mechanism 667 also has the function of a lifting device for the device holder 67.

Alternatively, the cables of the embodiment in FIG. 10 can be combined with the scissors mechanism 667 of the embodiment in FIG. 11. In this case, the scissors mechanism 667 acts primarily as a largely rigid guide for the device holder 67, which can accept horizontal forces and transmit them to the trolley 63, while the cables act as lifting devices for raising (and lowering) the device holder 67.

Contrary to FIG. 10, in FIG. 11 no cables are illustrated for transmitting electric power, electrical or optical signals, illuminating light or fluids between the container 68 and the device holder 67 and/or medical devices 69 onto the device holder 67. Cables can be foreseen as they were presented above with reference to FIG. 10. Alternatively, cables can run along the blades of the scissors mechanism 667 or can be affixed on them (in particular, at specific points).

Figure 12:
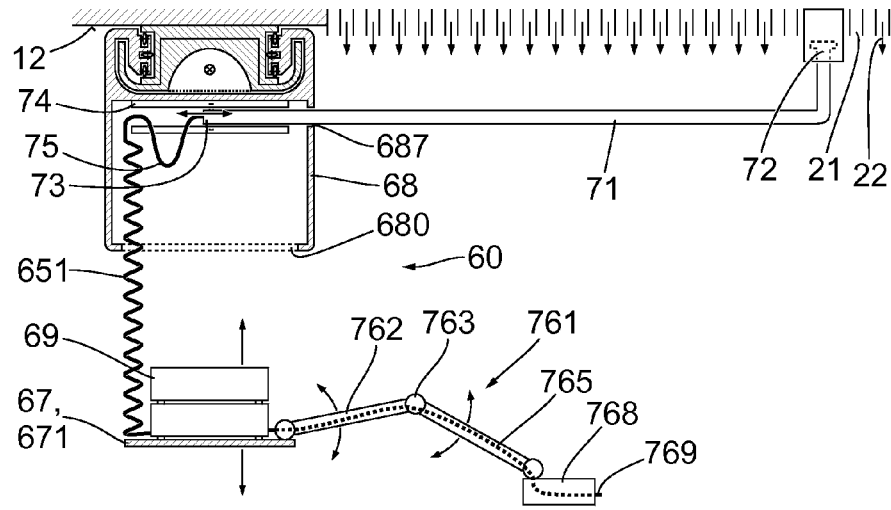
FIG. 12 shows a schematic depiction of a supply arm.

FIG. 12 shows a schematic depiction of a carrier apparatus 60, as it is presented above with reference to FIGS. 10 and 11, with a supply arm 71. The device holder 67 can be guided and raised corresponding to one of the embodiments discussed above with reference to FIGS. 10 and 11 or in other manner. Corresponding characteristics are therefore not shown in FIG. 12.

The supply arm 71 is connected at its radially inner end with the ceiling of the medical treatment facility via a joint 72, where the joint 72 makes it possible for the supply arm 71 to pivot around a vertical axis. The radially outer end 73 of the supply arm 71 extends through a lateral opening 687 into the container 68 and is fed there in one or more guide tracks 74. The guide tracks 74 make possible, in particular with a non-circular shape of the path determined by the tracks of the ceiling supply device, a length compensation or a compensation for a variation in the distance between the joint 72 and the container 68.

The radially outer end 73 of the supply arm 71 is connected with the upper end of the helical, extensible cable 651 described above with reference to FIG. 10, in particular by means of an elastic cable 75. In particular, the extensible cable 651 and the elastic cable 75 are formed by different portions of the same cable, which is configured as one piece. The elastic cable 75 makes it possible to slide the radially outer end 73 of the supply arm 71 in the container 68, in particular because of a slack loop, as indicated in FIG. 12, with variable geometric shape.

The supply arm 71, the elastic cable 75 and the extensible cable 651 are configured, in particular, to convey one or more different fluids to or from one of the devices 69 on the device holder 67. Therefore the joint 72, in particular, comprises an insulation by means of one or more shaft seals (often referred to as oil seals) or other insulations. Alternatively or in addition, the supply arm 71, the elastic cable 75 and the extensible cable 651 are configured to conduct electric current, electrical or optical signals or illuminating light. For this purpose, one or more corresponding cables can each be positioned on or—advantageously, as a rule—in the supply arm.

The supply arm is not configured to receive forces that exceed its own weight. The cross-section of the supply arm 71 can therefore be small and configured for a minimal disturbance of the vertical laminar flow field 22, for example by a tear-drop shape. A supply arm with the aforementioned properties can also be used with other carrier apparatuses than the one described with reference to FIGS. 10 through 12, for example with the one presented with reference to FIGS. 1 through 3. In addition, a supply arm 71 with the properties described here can be used to conduct electric power and electrical or optical signals to a projector, to a projection surface or to another display device or to one of the apparatuses described below with reference to FIGS. 13 and 14.

Also shown in FIG. 12 is a delivery arm 761 with several blades 762, which are connected by joints 763 with one another and jointedly connected with the device holder 67. The delivery arm 761 bears a satellite device 768 on its end that is remote from the device holder 67. On or in the delivery arm 761, one or more cables 765 can be mounted to transmit electric power, electrical or optical signals, illuminating light (for example, for endoscopes) and fluids. The cable or cables 765 couple one or more devices 69 on the device holder 67 with the satellite device 768. The satellite device 768 can provide operator controls or a user interface in order to control or monitor functions of one or more medical devices 69 on the device holder 67. In addition, the satellite device 768 can comprise one or more connections 769 on which, for example, illuminating light generated by one of the medical devices 69 is provided.

Because the delivery arm 761 is configured with one or more joints 763, the satellite device 768 can be positioned by medical staff in ergonomically optimal manner.

Contrary to the depiction in FIG. 12, the delivery arm 761, instead of with the device holder 67, can alternatively be jointedly mechanically connected with the container 68, with the supply arm 71, with the joint 72 of the supply arm 71, close to the joint 72 of the supply arm 71 with the ceiling of the medical treatment space 10 or with another attachment point. In the case of a mechanical attachment of the delivery arm 761 on the joint 72 of the supply arm 71, the delivery arm 761 can be rotatable or pivotable together with the supply arm 71 or independently of it. In the case of a mechanical attachment of the delivery arm 761 on the supply arm 71, the supply arm 71, unlike as described above, is configured as a girder for receiving or transmitting or diverting mechanical forces and moments.

The delivery arm 761 can be connected, merely in jointed, mechanical manner, with the device holder 67, with the container 68, with the supply arm 71, with the joint 72 of the supply arm 71, with the ceiling of the medical treatment facility 10 or with another attachment point. Alternatively, one or more linear translational degrees of freedom can be foreseen that, in particular, make possible a translation of the end of the delivery arm 761 that is at a distance from the satellite device 768 in the horizontal and/or vertical direction. For example, one or more steering devices can be provided that each make it possible to slide the end of the delivery arm that is at a distance from the satellite device 768 along a straight or curved path. In particular, the end of the delivery arm 761 that is at a distance from the satellite device 768 can be slidable along the supply arm 71.

Figure 13:
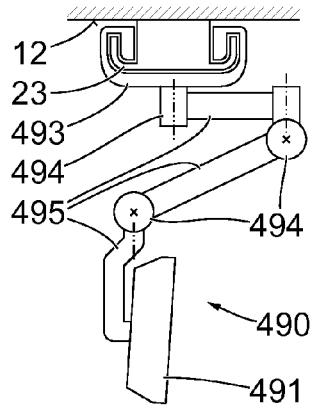
FIG. 13 shows a schematic depiction of a display device.

FIG. 13 shows a schematic depiction of a display device 490 that is distinguished from the display device that is formed by the projection surface 41 and projector 50, which are presented above with reference to FIGS. 1 through 3. A screen 491 is mechanically connected via several joints 494 and blades 495 with a trolley 493. The trolley can comprise characteristics of the trolley presented above with reference to FIGS. 4 through 9 and makes possible a movement along a ceiling supply system 23 on a ceiling surface 12. In the illustrated example, a blade 495 can pivot only in a horizontal plane or around a vertical axis, while another blade 495 can pivot around a vertical axis and around a horizontal axis.

Figure 14:
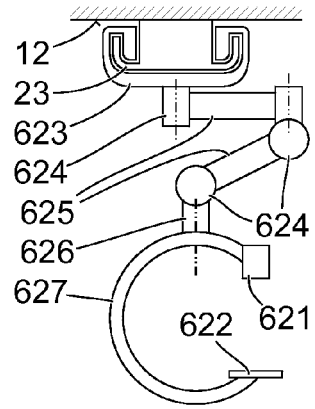
FIG. 14 shows a schematic depiction of an additional carrier apparatus.

FIG. 14 shows a schematic depiction of a carrier apparatus for carrying an x-ray source 621 and a locally sensitive x-ray detector 622 and/or an image sensor sensitive to x-ray radiation. The x-ray source 621 and x-ray detector 622 are rigidly interconnected via a C-shaped arc 627. The C-shaped arc 627 is connected with a trolley 623 by several joints 624 and several blades 625, 626. The trolley 623 comprises, in particular, characteristics that are described above with reference to FIGS. 4 through 9. The trolley 623 makes possible a movement along the path determined by tracks on the ceiling supply system 23 parallel to the ceiling surface 12.

In the embodiments in FIGS. 13 and 14, the blades 495 and joints 494 or the blades 625 and joints 624 constitute carrier apparatuses for the screen 491 or for the x-ray source 621 and x-ray detector 622. Because of the maneuverability by means of trolleys 493 or 623, the blades 495, 625 can be essentially shorter than conventional ones and thus disturb a vertical laminar flow field to a lesser degree than do conventional girders. In addition, the blades 495 and 625 can be positioned entirely outside the vertical laminar flow field, at least when not in use or when the screen 491 or x-ray source 621 and x-ray detector 622 are in resting position.

Figure 15:
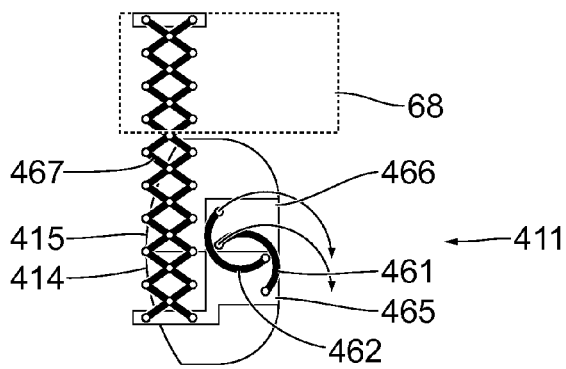
FIG. 15 shows a schematic depiction of a projection surface.
Figure 16:
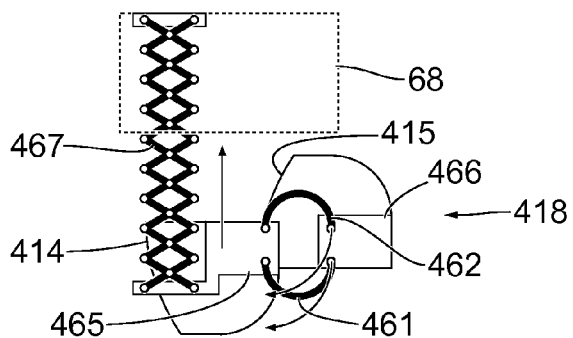
FIG. 16 shows an additional schematic depiction of the projection surface from FIG. 15.
Figure 17:
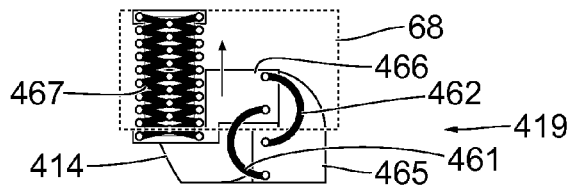
FIG. 17 shows an additional schematic depiction of the projection surface from FIGS. 15 and 16.

FIGS. 15 through 17 show schematic depictions of a projection surface 41 in an operating condition 411 (FIG. 15) and two additional conditions 418, 419. The planes of projection of FIGS. 15, 16 and 17 correspond to the planes of projection of FIGS. 1 and 4 through 14 or intersect them in a vertical straight line. Similarly as in the carrier apparatus presented above with reference to FIG. 11, a container 68 and a scissors mechanism 467 are foreseen. Instead of a device holder, a projection surface is foreseen that includes two areas 414, 415 and that can be vertically transported or moved by means of a scissors mechanism 467. The projection surface 414, 415 is domed and curved or comprises a positive Gaussian curvature. In particular, the projection surface 414, 415 has the shape of a portion of a spherical surface. The depictions in FIGS. 15 through 17 show the projection surface 414, 415 from the side, that is, a connecting line between a center point of the projection surface 414, 415 and a curvature center point of the projection surface 414, 415 is parallel to the planes of projection of FIGS. 15 through 17 and runs horizontally from left to right.

On the side turned toward the observer, every area 414, 415 of the projection surface is rigidly connected with a plate 465, 466. The plate 465 on the first area 414 of the projection surface and the plate 466 on the second area 415 of the projection surface are jointedly connected with one another via two connecting rods 461, 462. The connecting rods 461, 462 in the example illustrated in FIGS. 15 through 17 are each arch-shaped, in particular in the shape of a half arc. Corresponding plates and connecting rods are positioned on the sides of the areas 414, 415 of the projection surface that are not visible in FIGS. 15 through 17 and are turned away from the observer.

The mechanical coupling of the areas 414, 415 of the projection surface by the connecting rods 461, 462 makes possible essentially only a movement of the areas 414, 415 of the projection surface relative to one another, in which both areas do not modify their relative orientation.

In particular, the areas 414, 415 of the projection surface can be converted from the operating condition 411 shown in FIG. 15 by a movement that is indicated in FIG. 15 by arc-shaped arrows, into the condition shown in FIG. 16 and from there into the resting position shown in FIG. 17 by a movement that is indicated by arc-shaped arrows in FIG. 16. It can be recognized that the vertical extension of the projection surface 414, 415 in the resting position 419 is only half as large as in the operating condition 411.

After the transformation from operating condition 411 into resting condition 419 or simultaneously, the projection surface 414, 415 can be moved into the housing 68 indicated in broken lines by means of the scissors mechanism 467. In the housing 68, the projection surface 414, 415 can be protected from contamination and damage, particularly if, contrary to the depiction in FIGS. 15 through 17, a cap or cover closes the opening on the underside of the housing 68. Because of the transformation or conversion of the projection surface 414, 415 into resting position 419, the housing 68 can be markedly smaller than it would have to be if it were required to incorporate the projection surface 414, 415 in the operating condition 411. A cap or covering can be connected with the housing 68, in particular with the edge of the opening in the housing 68, by means of a joint. Alternatively, a cap or covering is positioned rigidly on the first portion 414 of the projection surface so that the opening in the housing 68 is closed when the projection surface in its resting condition has completely entered the housing 68.

Figure 18:
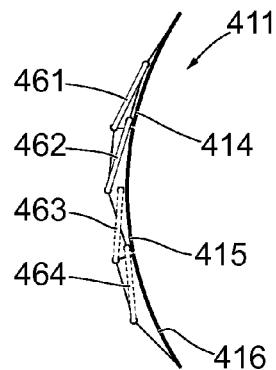
FIG. 18 shows a schematic depiction of an additional projection surface.
Figure 19:
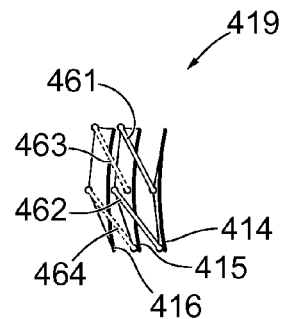
FIG. 19 shows an additional schematic depiction of the projection surface from FIG. 18.

FIGS. 18 and 19 show schematic depictions of an additional reshapable projection surface in an operating condition 411 (FIG. 18) and in a resting position 419 (FIG. 19). The planes of projection of FIGS. 18, 19 correspond in particular to the planes of projection of FIGS. 1 and 4 through 17. A corresponding transformation, however, is also a possible alternative in the horizontal direction, where horizontal planes of projection would yield corresponding images.

The projection surface comprises several areas 414, 415, 416 and has a dome-shaped, especially spherical, curvature. The areas 414, 415, 416 of the projection surface are jointedly connected with one another by connecting rods 461, 462, 463, 464. The distance of the joints between the first connecting rod 461 or the second connecting rod 462 and the first area 414 of the projection surface is smaller than the distance of the joints between the first connecting rod 461 or the second connecting rod 462 and the second area 415 of the projection surface. Alternatively or in addition, the connecting rods 461, 462 have different lengths between the joints. The same holds true for the second area 415 of the projection surface and the third area 416 of the projection surface as well as the third connecting rod 463 and the fourth connecting rod 464. As a result, the connecting rods and the joints form no parallelograms at the areas 414, 415, 416 of the projection surface. As is recognizable in a comparison of the operating condition 411 shown in FIG. 18 and the resting condition 419 shown in FIG. 19, this causes a non-parallel sliding of the areas 414, 415, 416 of the projection surface. While the areas 414, 415, 416 of the projection surface, corresponding to the curvature of the projection surface, have different orientations in the operating condition 411, in the resting condition 419 they are positioned essentially parallel to one another. This can make possible a tighter gripping of the projection surface or of its areas 414, 415, 416.

When the projection surface 414, 415, 416, similarly as with the embodiment in FIGS. 15 through 17, is to be stowed in a container in its resting condition 419 shown in FIG. 19, the parallelism of the areas 414, 415, 416 of the projection surface, recognizable in FIG. 19 can allow smaller dimensions for the container.

With a reshaping of the projection surface between its operating condition 411 and its resting condition 419, or with the corresponding sliding of the areas 414, 415, 416 in relation to one another, the connecting rod 462 bypasses the joint between the connecting rod 463 and the second area 415 of the projection surface. In addition, the connecting rod 463 bypasses the joint between the connecting rod 462 and the second area 415 of the projection surface. This is possible if the connecting rod 462 and its joint to the second area 415 of the projection surface on the one hand, and the connecting rod 463 and its joint to the second area 415 of the projection surface on the other hand, are not situated in one plane.

The depiction of the connecting rod 462 in shaded lines and of the connecting rod 463 in broken lines indicates that the connecting rods 462, 463 are not situated in one plane. For example, the plane in which the connecting rod 462 (and also, in particular, the connecting rod 461) can pivot and the plane in which the connecting rod 463 (and also, in particular, the connecting rod 464) can pivot are parallel to and at a distance from one another. More generally, the connecting rods 462, 463 must be disposed and formed in such a way that they do not block one another.

For this purpose, the connecting rods 462, 463 can be positioned in two different planes or, more generally, can be positioned and configured in such a way that the level or curved surfaces that they pass over do not intersect. Alternatively, the connecting rods 462, 463 can each be of arched configuration and positioned, for example, inside the same plane, similarly as with the example presented above with reference to FIGS. 15 through 17.

Figure 20:
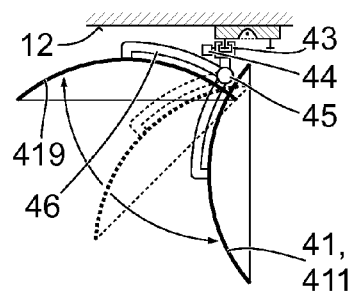
FIG. 20 shows a schematic depiction of an additional projection surface.

FIG. 20 shows a schematic depiction of a second embodiment of a projection surface 411 that resembles in some respects the projection surface presented above with reference to FIGS. 1 through 3. The plane of projection of FIG. 20 corresponds in particular to the plane of projection of FIGS. 1 through 3. The projection surface 411, similarly as presented above with reference to FIGS. 1 through 3, is movably attached to a track 31 by means of a trolley 43.

Contrary to the embodiment presented above with reference to FIGS. 1 through 3, a joint 45 is provided between the trolley 43 and the projection surface 41, in particular in the carrier 46. The joint 45 allows the projection surface 41 to pivot around a horizontal axis corresponding to the arched arrows that can be recognized in FIG. 2 between an operating condition 411 and a resting condition 419. In the resting condition 419, the projection surface 41 is situated immediately under the ceiling surface 12, where it does not restrict medical staff and its freedom of movement or does so less than in the operating condition.

Figure 21:
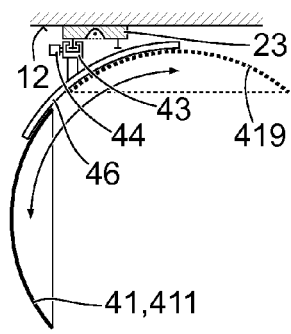
FIG. 21 shows a schematic depiction of an additional projection surface.

FIG. 21 shows a schematic depiction of an additional projection surface 41, which resembles in some respects the embodiment presented above with reference to FIGS. 1 through 3 and 20. The plane of projection of FIG. 21 corresponds in particular to the planes of projection of FIGS. 1 through 3 and 20.

Contrary to the embodiments in FIGS. 1 through 3 and 20, the projection surface 41 can slide along the carrier 46 configured as a curved track or linear guide. Because of the curvature of the projection surface 41 and the corresponding arch-shaped curvature of the carrier 46, the projection surface 41, guided by the carrier 46, can be slid or moved between an operating condition 411 and a resting condition 419 below the ceiling surface 12, corresponding to the arched arrow shown in FIG. 21. In this sliding of the projection surface 41, it is pivoted simultaneously around a horizontal axis.

Similarly as with the embodiment in FIG. 20, the projection surface 41 in the resting condition 419 below the ceiling surface 12 constitutes no obstacle or disturbance or restriction for medical staff and its freedom of movement. If the ceiling supply system 23 and thus the track of the ceiling supply system 23 that guides the trolley 43 is sufficiently far removed from the vertical laminar flow field 21 (see FIG. 1) that is not shown in FIG. 21, the projection surface 41 even in its resting condition 419 constitutes no disturbance for the vertical laminar flow field 21.

Figure 22:
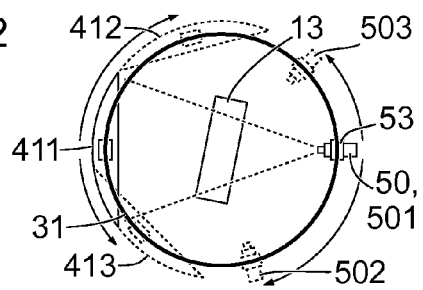
FIG. 22 shows an additional schematic depiction of the projection surface from FIGS. 20 and 21.

FIG. 22 shows an additional schematic depiction of a projection surface as is described above with reference to FIGS. 1 through 3, 20 and 21. The plane of projection of FIG. 22 corresponds in particular to the planes of projection of FIGS. 2 and 3. The projection surface 41 in its operating condition can be slid along the path determined by the circular track 31 between different operating positions 411, 412, 413. Thus, simultaneously, the projector 50 that can likewise be slid along the path determined by the track in the projection surface 41 can be brought into diametrically opposite working positions 501, 502, 503. In particular, at least either the projection surface 41 depending on the position of the projector 50, or the projector 50 depending on the position of the projection surface, is moved by means of power drive devices and guided by a control device in such a way that they are nearly diametrically opposite one another at all times.

Figure 23:
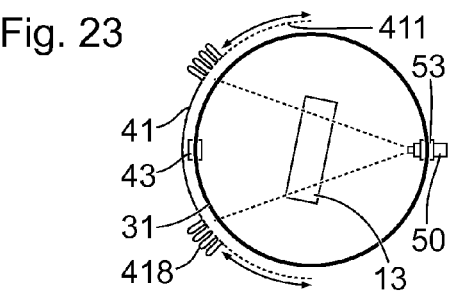
FIG. 23 shows a schematic depiction of an additional projection surface.

FIG. 23 shows a schematic depiction of an additional embodiment of a projection surface 41. The plane of projection of FIG. 22 corresponds in particular to the planes of projection of FIGS. 2, 3 and 22. The projection surface 41 and a projector 50 can be slid or moved by means of trolleys 43 or 53 along a path determined by a track, similarly as described above with reference to FIGS. 1 through 3 and 22. With the embodiment in FIG. 23, the projection surface 41 has the form of a segment of a cylinder in its operating condition, indicated only in dotted lines in FIG. 23. The axis of the cylinder is vertical or perpendicular to the plane of projection of FIG. 23, to the floor surface and to the ceiling surface of the medical treatment facility. The projection surface 41 can be folded together similarly as a curtain. In particular, the projection surface, from its lateral edges, corresponding to the arrows indicated in FIG. 23, can be shifted into an intermediate condition 418 depicted in a wavy line in FIG. 23 and further into a completely folded-together resting condition, which is not shown in FIG. 23. In the resting condition the projection surface 41 constitutes just a narrow bundle, which in addition can be folded away upward to the ceiling surface in order to avoid any impeding of medical staff and their freedom of movement. The projection surface 41 can be stabilized by vertical blades whose upper ends, for example, can be slid in a circular pattern on the track 31 or on a separate track that is attached to the trolley 43.

Figure 24:
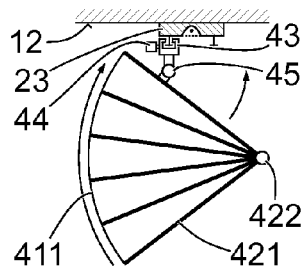
FIG. 24 shows a schematic depiction of an additional projection surface.
Figure 25:
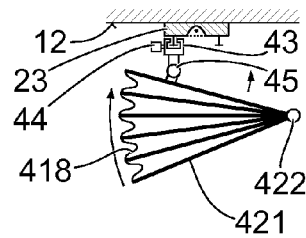
FIG. 25 shows an additional schematic depiction of the projection surface from FIG. 24.

FIGS. 24 and 25 show schematic depictions of an additional embodiment of a projection surface 41 in an operating condition 411 (FIG. 24) and in an intermediate condition 418 (FIG. 25) between the operating condition 411 and a resting condition that is not shown. The planes of projections of FIGS. 24 and 25 correspond, in particular, to the planes of projection of FIGS. 1, 4 through 9, 20 and 21. The projection surface 41, similarly as in the embodiments in FIGS. 1 through 3, 20 and 21, is movably attached by means of a trolley 43 to a track 31 of a ceiling supply system 23 parallel to a ceiling surface 12. Contrary to the embodiments in FIGS. 1 through 3, 20 and 21, the projection surface 41 is constituted by a surface of an elastic membrane, which can be tensed by blades 421 or brought into a predetermined shape. Each of the blades 421 is arched in shape, in particular in semi-circular shape. The ends of the blades 421 are brought together in two joints 422 opposite one another. In the operating condition 411 of the projection surface 41, shown in FIG. 24, the projection surface between two neighboring blades 421 comprises approximately the shape of a cylinder in each case. Altogether the projection surface 41 thus has nearly the shape of a portion of a spherical surface.

On the basis of the operating condition 411 of the projection surface 41, shown in FIG. 24, the blades can be folded up corresponding to the arrow shown at the left in FIG. 24 and can be pivoted upward corresponding to the arrow shown to the right in FIG. 24. By way of the intermediate condition 418 shown in FIG. 25, the projection surface can be shifted or transformed or reshaped into a resting condition, not shown. In this resting condition the projection surface 41 forms a narrow, arc-shaped bundle that is positioned below the ceiling surface 12. In this resting condition, which is not illustrated here, the projection surface only occupies a small space and constitutes no restriction for the medical staff and their freedom of movement.

Figure 26:
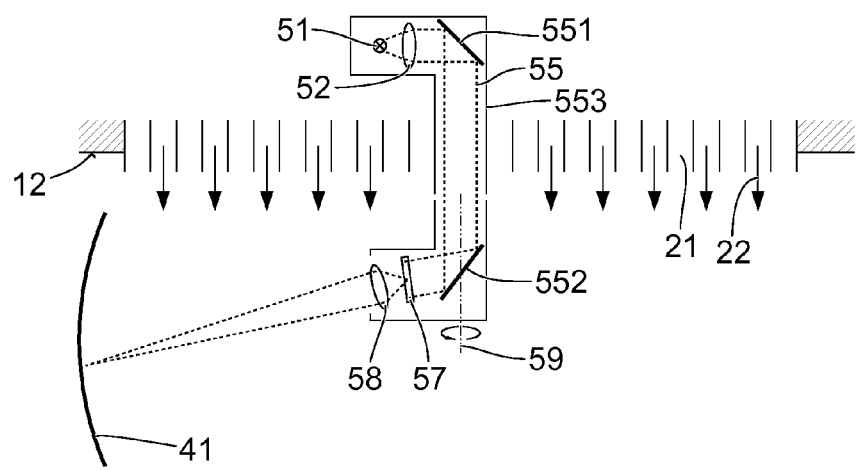
FIG. 26 shows a schematic depiction of a projection system.

FIG. 26 shows a schematic depiction of a projection system as an alternative to the projectors shown in FIGS. 1 through 3, 22 and 23. The plane of projection of FIG. 26 is, in particular, parallel to the planes of projection of FIG. 1. The projection system shown in FIG. 26 can be positioned in the center of the area of the ceiling surface occupied by the air nozzles 21 and, in particular, in the center of a circle, ellipse or oval that is formed by a ceiling supply system or one or more tracks parallel to the ceiling surface 12. As a result of this arrangement, during a movement of a projection surface along a path determined by the track, the projection system is not required to be slid but only rotated around a vertical axis 59. In order to disturb a vertical laminar flow field 22 as little as possible, the projection system is positioned at least partly above the ceiling surface 12.

The projection system includes in particular a light source 51, a collimator 52 and a first mirror 551 that are disposed above the ceiling surface 12, and a second mirror 552, a light modulator 57 and an imaging device 58 that are disposed below the ceiling surface 12. The imaging device 58 is, in particular, a lens, an object lens or a mirror system that has imaging properties. The collimator 52 collimates the light generated by the light source 51. The prevailingly parallel light is directed by the two mirrors 551, 552 onto the light modulator 57. The light modulator 57 is, for example, an LCD component. The image generated by the light modulator 57 is imaged by the imaging device 58 onto a projection surface 41. The collimator 52 and the mirrors 551, 552 as well as a tube 553 between these two define the cross-section of a beam path 55 to transmit or guide light of the light source 51 to the light modulator 57.

By rotating the second mirror 552, light modulator 57 and imaging device 58 around a vertical pivot axis 59, the direction in which an image is projected can be adjusted to the site of the projection surface 41. By tipping and sliding the light modulator 57, imaging device 58 and second mirror 552 as well as individual components not shown in FIG. 26 (in particular, lenses and lens groups) of the imaging device 58, it becomes possible to adjust the projection direction as well as the position and the spatial shape of the image generated by the imaging device 58 to the site, the orientation and the shape of the projection surface 41. In addition, the image of the light modulator 57 generated by the imaging device 58 can be reshaped by sliding and tipping the light modulator 57 and imaging device 58, depending on the position of an observer, in such a way that the observer perceives the image on the projection surface 41 without distortion, in particular parallel straight lines in the image as parallel and right angles as right angles.

Contrary to the depiction in FIG. 26, the light modulator 57 or the light modulator 57 and at least a part of the imaging device 58 can be disposed above the ceiling surface 12. Thereby, the measuring of the components of the projection system disposed below the ceiling surface 12 and the resulting disturbances of the vertical laminar flow field 22 can be further reduced.

IF the light modulator 57 and the imaging device 58, otherwise than as shown in FIG. 26, cannot pivot together around the vertical pivot axis 59, a rotation of the imaging device 58 around the vertical pivot axis 59 can cause a tipping of the projected image. This is especially true when the light modulator 57 is disposed in stationary manner above the ceiling surface 12. In compensation, it is possible to foresee a rotation of the light modulator around the local optical axis of the projection system, and in particular around its surface normal, simultaneously with the rotation of the imaging device 58 around the vertical pivot axis 59. Also possible is a corresponding mechanical coupling between the imaging device 58 and the light modulator 57 or a corresponding logical coupling with a mechanical control device that couples both movements.

As an alternative, between the fixed light modulator 57 and the imaging device 58 that can pivot around the vertical pivot axis 59, it is possible to provide a device for erecting an image, for example an arrangement of one or more prisms. This device to erect the image is rotated by a mechanical or logical coupling simultaneously with a pivoting of the imaging device 58 around the vertical pivot axis 59, in such a way that the angle speeds stand in a fixed ratio to one another.

Alternatively, the projection system or a device controlling the light modulator 57 can be configured in order to rotate the modulation pattern appearing on the light modulator 57, corresponding to a pivot movement of the imaging device 58, around the vertical pivot axis 59.

Figure 27:
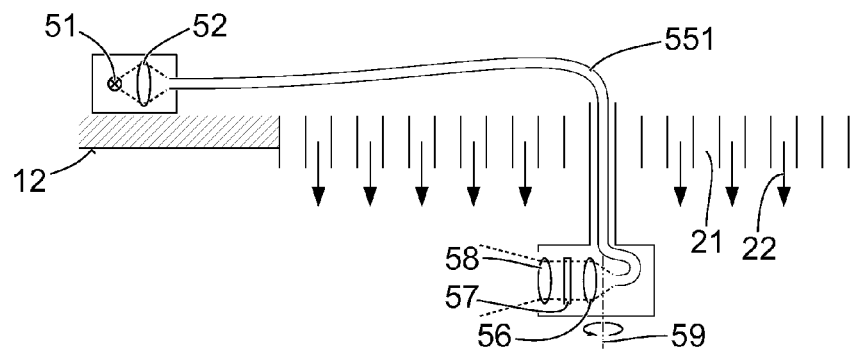
FIG. 27 shows a schematic depiction of an additional projection system.

FIG. 27 shows a schematic depiction of an additional projection system. The plane of projection of FIG. 27 corresponds to the plane of projection of FIG. 26. An imaging device 58, similarly as with the embodiment of FIG. 26, is disposed below the ceiling surface 12, and a light source 51 is disposed above the ceiling surface 12. Light from the light source 51, however, is not transmitted by means of mirrors but rather by means of a light conductor cable 557 from the light source 51 over the ceiling surface 12 to a light modulator 57 and to the imaging device 58. To switch the light generated by the light source 51 into the light conductor cable 557, a converging lens 52 is provided. The light switched out of the light conductor cable 557 is collimated by a collimator 56 and then modulated by the light modulator 57. The light modulator is imaged by the imaging device 58 onto a projection surface that is not shown in FIG. 27.

Similarly as presented above with reference to FIG. 26, it is possible to adjust the projection direction, the position and the shape of the projection surface by rotating the collimator 56, the light modulator 57 and the imaging device 58 around a vertical pivot axis 59 and pivoting around a horizontal axis not shown in FIG. 27 as well as by tipping and sliding the light modulator 57 and imaging device 58 or components of the imaging device 58 with respect to one another. It is also possible to reshape the image to generate an undistorted impression in an observer. The latter is possible with both embodiments of FIGS. 26 and 27, alternatively or in addition, by modifying the signal that controls the light modulator 57.

With most of the embodiments presented above with reference to FIGS. 1 through 3 and 15 through 25, it is possible in place of projection surfaces 41 to provide image surfaces that, for example, are configured as rigid or flexible OLED displays in order to emit light and to display information without requiring a projector. Provided that the image surface is not elastic as, for example, in the embodiments in FIGS. 23 through 25, the image surface alternatively can include a rigid liquid crystal display (LCD display), a rigid plasma image screen or another rigid screen.

Figure 28:
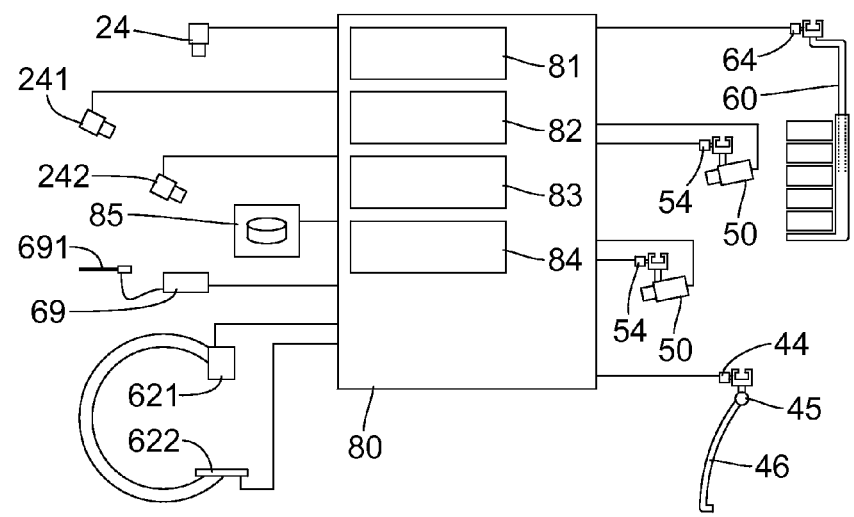
FIG. 28 shows a schematic depiction of a steering device.

FIG. 28 shows a schematic depiction of a control device 80 to control one or more functions of the systems, apparatuses and devices that are presented above with reference to FIGS. 1 through 27. The control device is, in particular, coupled with the room camera 24 described above with reference to FIG. 1 and additional room cameras 241, 242, an external image storage device 85, an endoscopy system 69 with an endoscope 691 and a locally sensitive x-ray detector or x-ray sensitive image sensor 622, in order to receive images from them. In addition, the control device 80 can be coupled with the room cameras 24, 241, 242, the endoscopy system 69, 691, the external image storage device 85, an x-ray source 621 and the x-ray sensitive image sensor 622 in order to adjust their operating parameters, to move, pivot and control them.

The control device 80 is also coupled with one or more projectors 50 in order to emit image signals to the projectors 50. In addition, the control device 80 is coupled with power drive devices 44, 54, 64 at projection surfaces, projectors and carrier apparatuses in order to control movements of trolley along one or more tracks as well as translational movements, in particular vertical translation movements, pivoting and rotating movements. The power drive devices 44, 54, 64 and the control device 80 thereby constitute positioning devices to position projection surfaces, projectors, carrier apparatuses or medical devices The control device includes an internal image source 81, a gesture recognition device 82 that is coupled in particular with the room cameras 24, 241, 242 or other sensors, a positioning device 83 and a distortion corrector 84. The gesture recognition 82, positioning 83 and distortion correction 84 can each be achieved partly or completely by separate analog or digital electronic hook-up or partly or completely by software or firmware.

The control device 80 is configured in particular to adjust one or more projection surfaces and one or more projectors or projection systems depending on gestures of medical staff and/or depending on a phase in a work sequence and/or depending on a position or a viewing angle of medical staff, in such a way that medical staff can work under ergonomically favorable conditions. In addition the control device 80 is configured to move or configure projection surfaces, projectors, cameras, carrier apparatuses and other mechanically movable devices in such a way that they do not impede or harm one another and medical staff, and so that a projector and a projection surface, for example, are essentially positioned opposite one another.

What is claimed is:

1. A display apparatus, having:
   an image surface to display medical information in a medical treatment facility,
   such that the image surface is configured to convert by reshaping from an operating condition into a resting condition and vice versa, and
   the image surface has a substantially positive Gaussian curvature in the operating condition, the image surface comprising a plurality of areas that in the operating condition each have a concave shape
   wherein the image surface is mounted to a ceiling.

2. The display apparatus according to claim 1, wherein the image surface is a projection surface.

3. The display apparatus according to claim 2, in addition having:
   a projection system to project a depiction of information onto the projection surface, wherein the projection system includes a light source, a light modulator and an imaging device such that the light source is set apart from at least one of the imaging device or the light modulator.

4. The display apparatus according to claim 1, wherein the image surface is constituted by a light-emitting image screen.

5. The display apparatus according to claim 1, wherein in the operating condition the areas form the image surface and in the resting condition the areas are disposed at a distance from one another.

6. The display apparatus according to claim 1, in addition having a rectification device to reshape an image that is to be depicted by the image surface in such a way that the image is perceived by an observer at a predetermined location as non-distorted.

7. The display apparatus according to claim 1, in addition having:
   a rectification device with an input for receiving a signal that depends on a position of an observer, such that the rectification device is configured in order to control the display apparatus depending on the position of the observer.

8. The display apparatus according to claim 1, in addition having:
   a container that is configured to receive the image surface in a resting position.

9. A display apparatus for displaying medical information in a medical treatment facility, having:
   an image surface to display information, such that the image surface is configured to convert by reshaping from an operating condition into a resting condition and vice versa, and the image surface has a substantially positive Gaussian curvature in the operating condition, the image surface comprising a plurality of areas that in the operating condition each have a concave shape, and
   a container that is configured to receive the image surface in a resting position,
   wherein the container is attached in a movable manner to a track on a ceiling surface of a medical treatment facility.

10. The display apparatus according to claim 9, in addition having:
    a power drive device to move the image surface between the resting position inside the container and an operating position in which information can be depicted visibly for medical staff on the image surface.

11. A display apparatus for displaying medical information in a medical treatment facility, having:
    an image surface to display information, such that the image surface is configured to convert by reshaping from an operating condition into a resting condition and vice versa, and the image surface has a substantially positive Gaussian curvature in the operating condition, the image surface comprising a plurality of areas that in the operating condition each have a concave shape,
    wherein the image surface is a projection surface that can slide along a path determined by a track device and wherein the display apparatus in addition includes a projector that can slide along the path to project a depiction of information onto the projection surface and a positioning device to establish the positions of the projector and projection surface on the path, such that the positioning device is configured to position the projector and the projection surface at positions essentially opposite one another on the path determined by the track device.

12. A display apparatus for displaying medical information in a medical treatment facility, having:
    an image surface to display information, such that the image surface is configured to convert by reshaping from an operating condition into a resting condition and vice versa, and the image surface has a substantially positive Gaussian curvature in the operating condition, the image surface comprising a plurality of areas that in the operating condition each have a concave shape,
    the image surface being a projection surface, and
    a projection system to project a depiction of information onto the projection surface, wherein the projection system includes a light source, a light modulator and an imaging device such that the light source is set apart from at least one of the imaging device or the light modulator,
    wherein the light source is mounted above a ceiling surface of the medical treatment facility, and at least one of the imaging device or the light modulator is mounted below the ceiling surface.

13. A display apparatus for displaying medical information in a medical treatment facility, having:
    an image surface to display information, such that the image surface is configured to convert by reshaping from an operating condition into a resting condition and vice versa, and the image surface has a substantially positive Gaussian curvature in the operating condition, the image surface comprising a plurality of areas that in the operating condition each have a concave shape, and
    a foldable structural device and an elastic membrane that is held by the foldable structural device and forms the image surface.

14. The display apparatus according to claim 13, wherein the elastic membrane can be removed from the foldable structure and can be sterilized separately.

* * * * *